(12) United States Patent
McIvor et al.

(10) Patent No.: US 6,213,988 B1
(45) Date of Patent: Apr. 10, 2001

(54) INTRODUCER WITH EXTERNAL HEMOSTASIS CLIP

(75) Inventors: Michael E. McIvor, St. Petersburg, FL (US); Mary M. Morris, Mounds view, MN (US); Judith Betz, Blaine, MN (US); Timothy G. Laske, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/021,558

(22) Filed: Feb. 10, 1998

(51) Int. Cl.[7] .......................... A61M 5/00; A61M 5/178; A61M 31/00
(52) U.S. Cl. ................... 604/264; 604/164; 604/165.01; 604/506
(58) Field of Search ................................... 604/264, 164, 604/165, 166, 160, 161, 172

(56) References Cited

U.S. PATENT DOCUMENTS

| | | |
|---|---|---|
| 4,166,469 | 9/1979 | Littleford . |
| 4,306,562 | 12/1981 | Osborne . |
| 4,596,559 | 6/1986 | Fleischhacker . |
| 4,744,788 | * 5/1988 | Mercer, Jr. .............................. 604/49 |
| 5,098,393 | 3/1992 | Amplatz et al. . |
| 5,312,355 | 5/1994 | Lee . |
| 5,672,158 | 9/1997 | Okada et al. . |
| 5,730,756 | * 3/1998 | Kieturakis et al. ................... 606/190 |
| 5,755,693 | * 5/1998 | Walker et al. ........................ 604/160 |

* cited by examiner

Primary Examiner—Richard Seidel
Assistant Examiner—Michael J. Hayes
(74) Attorney, Agent, or Firm—Reed A. Duthler; Harold R. Patton; Girma Wolde-Michael

(57) ABSTRACT

An introducer of the type employing an elongated introducer sleeve for receiving a catheter or lead body and an associated hemostasis clamp including a clamping member configured to engage the outer circumference of the introducer sleeve. The clamp is provided with a mechanism for maintaining the clamping member in engagement with said outer circumference of the sleeve to compress the outer circumference of the sleeve around a catheter or lead body inserted therethrough. In some embodiments the clamp takes the form of a hinged clamp provided with two jaws each having a recess adapted to engage a portion of the other circumference of the introducer sleeve. In other embodiments the clamp takes the form of interacting ramped members. The clamp is maintained in engagement with the sleeve either resiliently or by means of a latch.

12 Claims, 4 Drawing Sheets

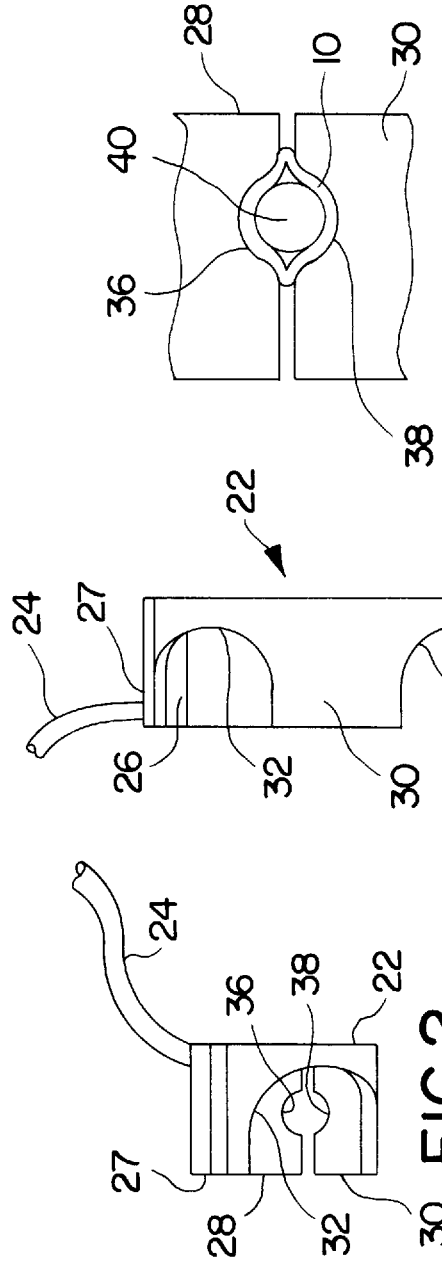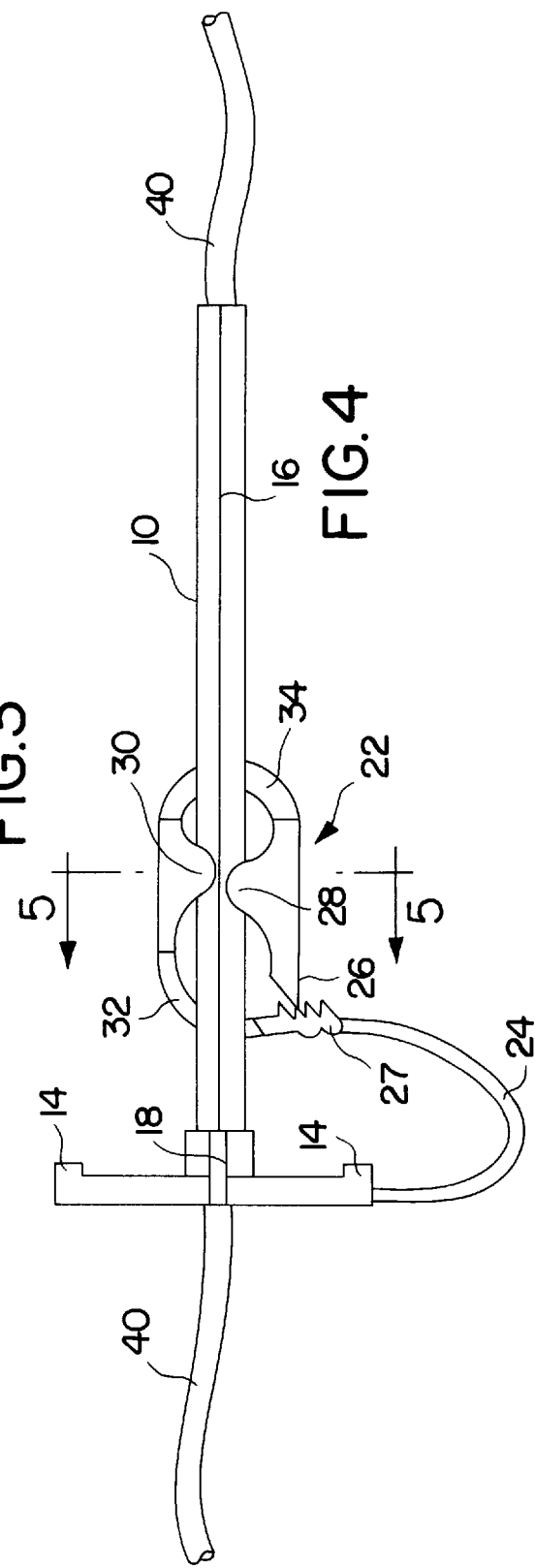

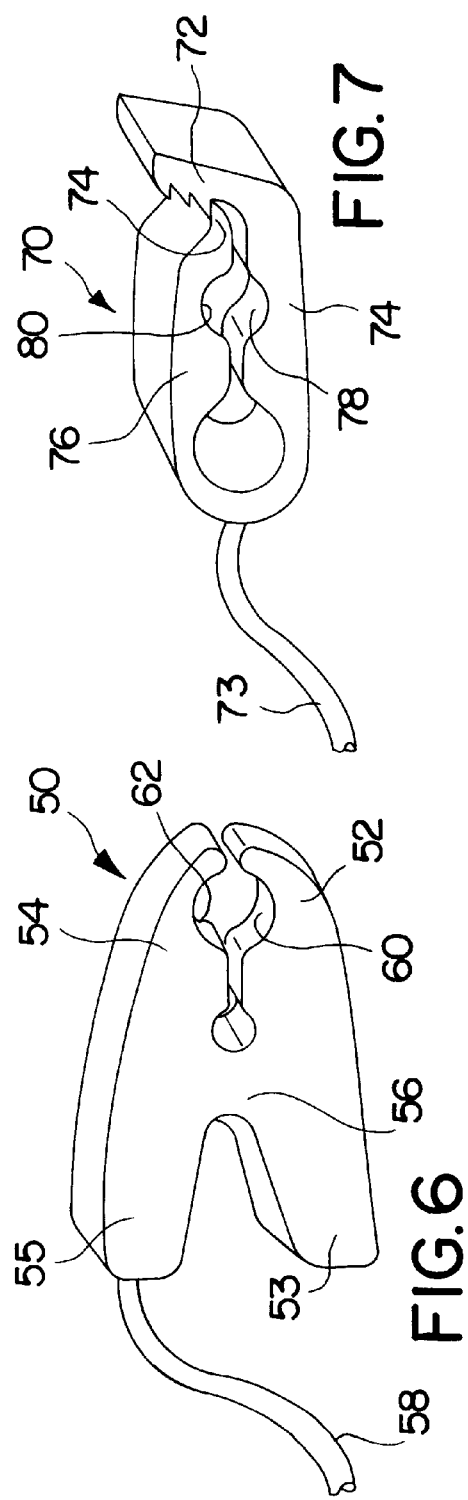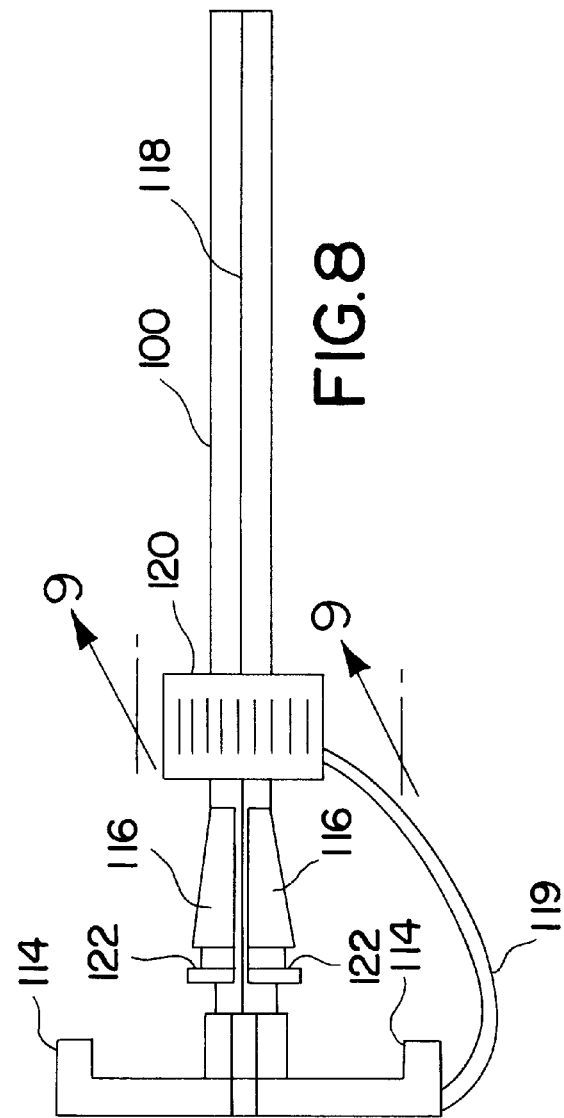

ative sleeve by means of a plastic lanyard 24. The clamp 50 is coupled to an associated intro-

INTRODUCER WITH EXTERNAL HEMOSTASIS CLIP

BACKGROUND OF THE INVENTION

Introducers for implantable leads and catheters typically include a dilator and an associated introducer sleeve, through which the lead or catheter is to be inserted. Conventional designs of lead and catheter introducers are disclosed in U.S. Pat. No. 4,306,562 issued to Osborne, U.S. Pat. No. 4,596,559 issued to Fleischhacker and U.S. Pat. No. 4,166,469 issued to Littleford. In conjunction with such introducers, it has become common to include a hemostasis valve. Introducers including hemostasis valves are illustrated in U.S. Pat. No. 5,672,158 issued to Okada et al., U.S. Pat. No. 5,098,393 issued to Amplatz et al. and U.S. Pat. No. 5,312,355 issued to Lee. In all such cases, the hemostasis valve engages the circumference of the lead or catheter to be introduced.

SUMMARY OF THE INVENTION

The present invention is directed toward a substantially simplified lead or catheter introducer including an external hemostasis clip as a substitute for the more conventional hemostasis valve. The hemostasis clip, rather than engaging the circumference of the lead or catheter compresses the introducer sleeve around the external circumference of the lead or catheter. In its preferred embodiments, the clip is configured so that it may be removed from the sleeve, prior to the sleeve being removed from the catheter or lead body by means of either slitting or tearing the introducer sleeve.

BRIEF DESCRIPTION OF THE DRAWINGS

FIG. 2 is an end plan view of an introducer clip according to the present invention.

FIG. 3 is a bottom plan view of a first embodiment of an introducer clip according to the present invention.

FIG. 4 is a side plan view of an introducer, including the hemostasis clip of the present invention, impressing the introducer around the body of a lead or catheter passing through the introducer sleeve.

FIG. 5 is a cross-sectional view through the introducer and lead combination of FIG. 4, showing compression of the introducer sleeve around the lead body.

FIG. 6 is a perspective view of an alternative embodiment of a hemostasis clip according to the present invention.

FIG. 7 is a perspective view of a second alternative hemostasis clip according to the present invention.

FIG. 8 is a side plan view of an alternative embodiment of an introducer according to the present invention employing a hemostasis clip which includes compression members mounted permanently to the introducer sleeve.

DETAILED DESCRIPTION OF THE PREFERRED EMBODIMENTS

Figure 1:
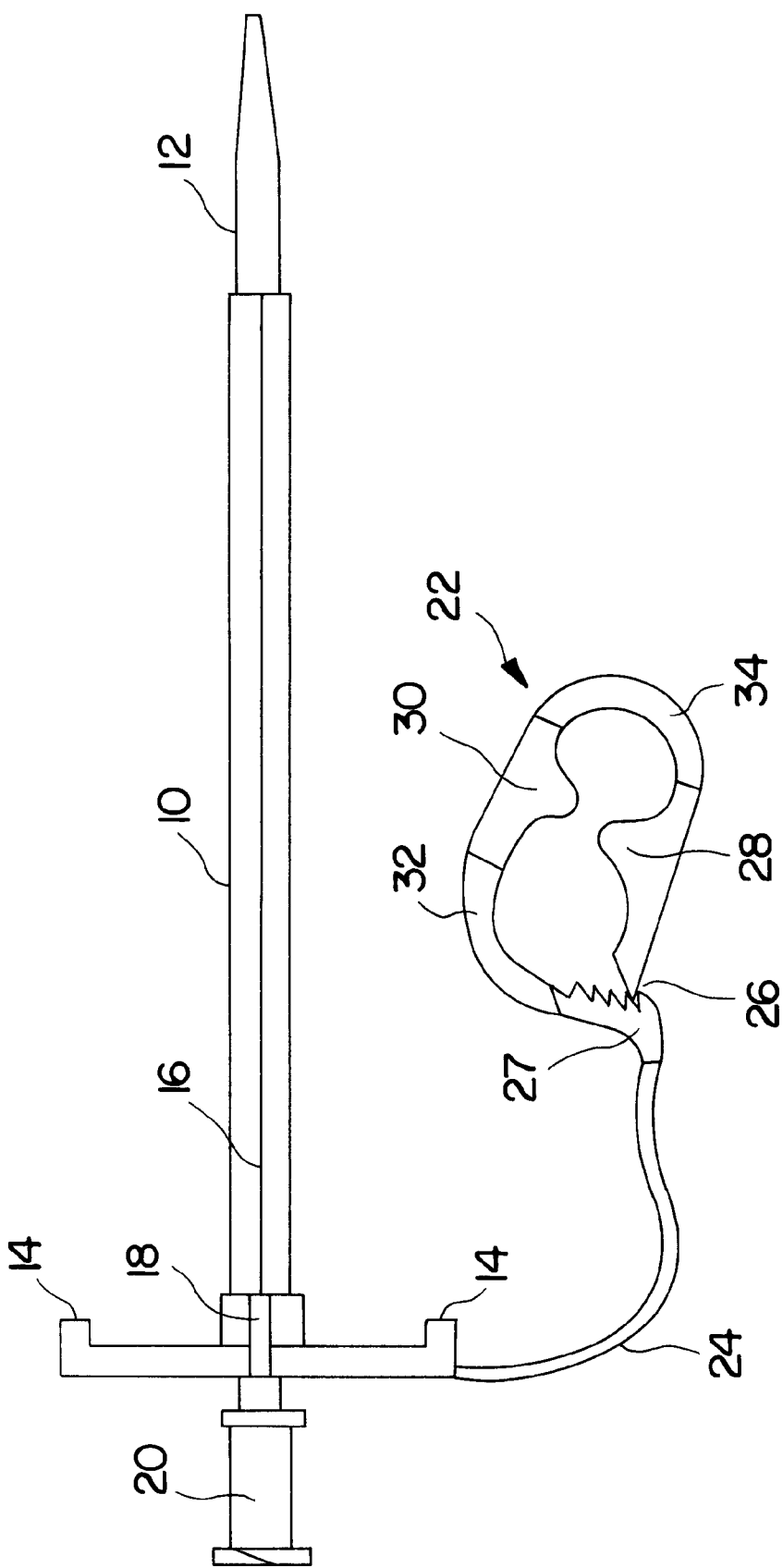
FIG. 1 is a plan view of an introducer including the hemostasis clip according to the present invention.

FIG. 1 is a plan view of the first embodiment of an introducer and associated hemostasis clip according to the present invention. The introducer includes an introducer sleeve 10 which is provided with weakened zones 16 extending the length of the introducer sleeve on opposite sides of the sleeve, allowing the sleeve to be separated into two pieces and removed from the catheter or lead passed therethrough as disclosed in U.S. Pat. No. 4,166,469 issued to Littleford, and incorporated herein by reference in its entirety. At the proximal end of sleeve 10 are mounted handles 14 which are employed to separate the sleeve 10 so that it may be removed from the lead or catheter passed therethrough. Handles 14 are molded of a single plastic component provided with weakened zones 18 on either side of the handle assembly, facilitating separation of handles 14. A dilator 12 is illustrated inserted into sleeve 10. A luer lock fitting 20 is mounted to the proximal end of the dilator.

A hemostasis clip 22 is coupled to one of the handles 14 by means of a plastic lanyard 24. Clip 22 and handles 14 and lanyard, may all be molded of a single piece of plastic or may be assembled of multiple plastic components. Clip 22 in general resembles a tubing clamp of the type typically employed to clamp off medical tubing, and includes upper and lower jaw members 28 and 30, connected by means of a recessed area 34. At one end of the upper jaw 28 is located a first latching member 26 which engages a corresponding latching member 27 coupled to lower jaw 30 by means of a second recessed area 32. In use, the sleeve 10 is clamped between upper and lower jaws 28 and 30, and passes through recessed areas 32 and 34. The structure in operation of clamp 22 is discussed in more detail below.

FIG. 2 is a proximal end view of clamp 22. In this view, the proximal surface of the second latching member 27 is visible along with the configuration of the first recessed area 32, through which the introducer sleeve 10 (FIG. 1) will pass. In this view, it can be seen that upper and lower jaw members 28 and 30 are each provided with a recess, 38 and 36, which are intended to engage the sleeve 10 (FIG. 1) around its outer circumference.

FIG. 3 is a bottom plan view of hemostasis clip 22, further illustrating the configuration of recessed areas 32 and 34 through which the introducer sleeve 10 passes. The lower surfaces of latching members 26 and 27 and lanyard 24 are also visible in this view.

FIG. 4 illustrates the hemostasis clamp 22, clamped around introducer sleeve 10, compressing it around the body of catheter or lead 40, passing therethrough. The introducer sleeve 10 is located within the recesses 36 and 38 (FIG. 2) and is compressed therein around the outer circumference of lead or catheter 40. Latching members 26 and 27 maintain compression of the upper and lower jaws 28 and 30, respectively. In this view it can also be seen how introducer sleeve 10 passes through recessed areas 32 and 34. All other numbered elements correspond to those illustrated in FIG. 1.

FIG. 5 is a cross-sectional view through the combination of the introducer and catheter or lead illustrated in FIG. 4. In this view it can be seen how the introducer sleeve 10 is compressed around lead body 40 to provide a seal. While the seal is not air tight, it is sufficient to prevent any significant flow of blood proximally through the introducer sleeve 20. All other labeled components correspond to those illustrated in FIGS. 2 and 4. In addition, the clamp 22 may also be employed to clamp the introducer sleeve 10 against itself to provide a seal, by clamping the sleeve in region 39, between the linear portions of the jaws 28 and 30.

FIG. 6 is a perspective view of an alternative embodiment of a hemostasis clamp appropriate for use with the present invention. The clamp 50 is coupled to an associated introducer sleeve by means of a lanyard 58 and includes upper and lower jaws 52 and 54 which carry corresponding recesses 60 and 62 for engaging the outer circumference of the associated introducer sleeve. The clamp is provided with two handle portions 53 and 55 which when compressed cause flexion of resilient hinge portion 56 of the clamp, allowing the clamp to be opened. Optionally, an additional spring may be provided located between handles 53 and 55 to assist in compression of the upper and lower jaws 54 and 52 around the introducer sleeve.

FIG. 7 is a perspective view of a second alternative embodiment of as hemostasis clip for use in conjunction with the present invention. Hemostasis clip 70 is attached to an associated introducer by means of lanyard 73 and includes upper and lower jaws 76 and 74, respectively, which each include a corresponding recess 80 and 78, respectively for engaging the outer surface of the associated introducer sleeve. The clamp is provided with latching members 72 and 74 corresponding to latching members 27 and 26, respectively of the clamp illustrated in FIGS. 1 through 5.

The alternative embodiments illustrated in FIG. 6 and FIG. 7 work functionally precisely in the manner of the clamp illustrated in FIGS. 1 through 5 with the exception that the hinge mechanism connecting the two jaws of the clamps operates perpendicular of the hinging mechanism of the clamp illustrated in FIG. 4. In use, after the lead is passed through the introducer sleeve, the associated clamp, according to any of the preceding three embodiments is simply clamped around the introducer sleeve to compress it against the lead or catheter body. When it is time for the introducer sleeve to be removed, the clamp is simply released and removed from the introducer sleeve allowing the introducer to be slit or torn in a conventional manner.

FIG. 8 is a plan view of an additional alternative embodiment of a clamping mechanism for use in conjunction with an introducer according to the present invention. In this embodiment, the introducer sleeve 100 is provided with two ramped, semi-conical members 116, located on either side of the weaken zones 118, on either side of the sleeve. Ramped members 116 are each provided with a circumferential groove 122 which engages a corresponding internal circumferential projection in clamping ring 120. The interior surface of clamping ring 120 is provided with a corresponding conical, ramped surface which, on being slid proximally along ramped members 116 compresses introducer sleeve 100 around the circumference of a lead or catheter body inserted therethrough. The ramped members 116 and clamping ring 120 are configured so that a tight seal around the lead or catheter body is accomplished when the internal circumferential projection within clamping ring 120 engages grooves 122. Clamping ring 120 can be detached from ramped members 116 by simply sliding it distally, disengaging the internal projection therein from grooves 122. Clamping ring 122 is coupled to handles 114 by means of a lanyard 119. Removal of clamping ring 120 from sleeve 100 prior to slitting or tearing of sleeve 100 may be accomplished by configuring anchoring ring 120 as a "C" shaped ring which may be expanded to allow removal from introducer sleeve 100 or by configuring anchoring ring 120 as a hinged ring with a latch, which may be unlatched and opened, allowing removal of clamping ring 120 from introducer sleeve 100. The configurations of ramped members 116 and clamping ring 120 are discussed in more detail below.

Figure 9:
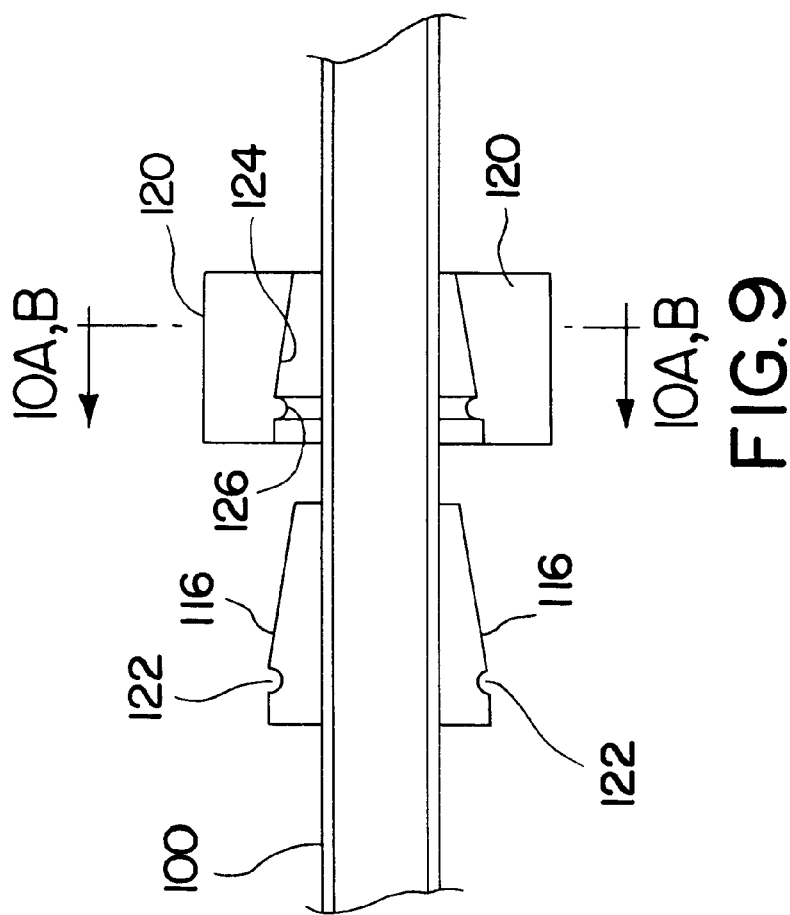
FIG. 9 is a sectional view through the introducer of FIG. 8 illustrating the configuration of the compression members and an associated compression ring employed to compress the introducer sleeve around a lead body or catheter body passed therethrough.

FIG. 9 is a sectional view the portion of the introducer illustrated in FIG. 8, including ramped members 116 and clamping ring 120. In this view the configuration of the internal, conically ramped surface 124 of clamping ring 120 and the configuration of the circumferential interior projection 126 is visible. In use, clamping ring 120 is simply slid proximally until internal projections 126 engage indentations 122, holding introducer sleeve 100 clamps tightly around the catheter or lead body passing therethrough.

Figure 10A:
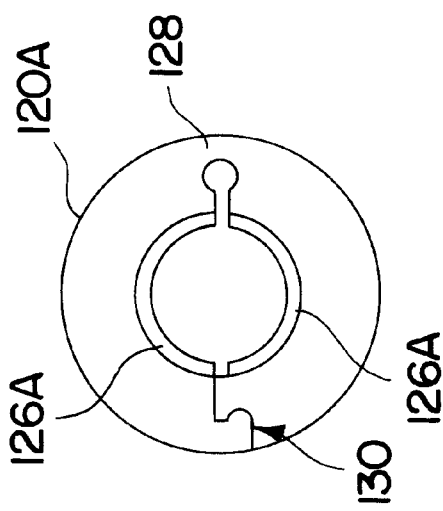
FIGS. 10a and 10b are cross-sectional views through alternative embodiments of the compression ring illustrated in FIG. 9.

FIG. 10A is a cross-sectional view through a first embodiment of clamping ring 120. In this embodiment, clamping ring 120A is formed to provide an integral hinge 128 and a releasable latch 130. On release of latch 130 by compression of clamping ring 120A, the ring may be opened at hinged portion 128 and removed from the associated introducer sleeve. Internal projection 126A is also visible in this view.

Figure 10B:
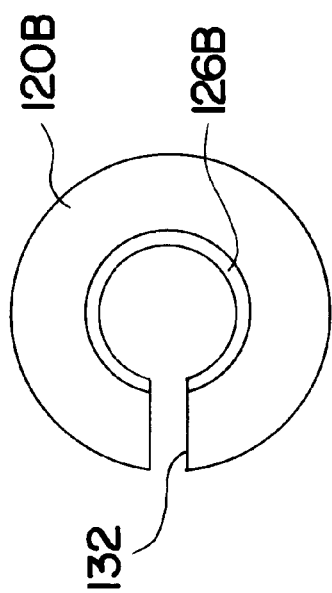

FIG. 10B is a cross-sectional view through a second embodiment of a clamping ring 120B according to the present invention. In this embodiment, the clamping ring 120B is formed as a "C" shaped ring, having a lateral opening 132. Removal of the clamping ring 120B from the associated introducer sleeve is accomplished by simply spreading apart the ends of the locking ring 120B adjacent opening 132 and removing the ring from the introducer sleeve. Internal projection 126B is also visible in this view.

In conjunction with the above disclosure, a number of specific alternative mechanisms for allowing compression of an introducer sleeve around a catheter or lead body inserted therethrough are disclosed to illustrate the present invention. These illustrated embodiments are intended to be merely exemplary of the invention, rather than limiting, in conjunction with the claims which follow.

In conjunction with the above specification, we claim:

1. An introducer, comprising:
   an elongated introducer sleeve for receiving a catheter or lead body;
   a hemostasis clamp including a clamping member configured to engage the outer circumference of the introducer sleeve and comprising means for maintaining said clamping member in engagement with said outer circumference of said introducer sleeve to compress said outer circumference of said introducer sleeve around a catheter or lead body inserted therethrough; and
   a lanyard coupling the clamp to the introducer sleeve.

2. An introducer according to claim 1 wherein said clamp is provided with first and second jaws each having a recess adapted to engage a portion of the outer circumference of the introducer sleeve.

3. An introducer according to claim 2 wherein said first and second jaws are coupled to one another by means of a hinge.

4. An introducer according to claim 1 or claim 2 wherein said clamp is provided with a latch which maintains said clamping member in engagement with said introducer sleeve.

5. An introducer according to claim 1 wherein said clamp is provided with a resilient member which maintains said clamping member in engagement with said introducer sleeve.

6. An introducer, comprising:
   an elongated introducer sleeve for receiving a catheter or lead body; and
   an associated hemostasis clamp including a clamping member configured to engage the outer circumference of the introducer sleeve and comprising means for maintaining said clamping member in engagement with said outer circumference of said introducer sleeve to compress said outer circumference of said introducer sleeve around a catheter or lead body inserted therethrough; said clamping member having a first ramped member attached to said introducer sleeve and extending around a portion of the outer circumference of said sleeve and said maintaining means having a second ramped member slidable along said first ramped member.

7. An introducer according to claim 6 wherein said clamp is provided with a latch which maintains said clamping member in engagement with said maintaining means.

8. A method of introducing a catheter or lead comprising:

inserting said catheter or lead through an introducer sleeve;

compressing said introducer sleeve around said lead to provide a hemostatic seal; and thereafter uncompressing said sleeve and removing said introducer sleeve from said lead or catheter.

9. A method according to claim 8 wherein said compressing step comprises compressing said introducer sleeve with a clamp.

10. A method according to claim 9 wherein said compressing step comprises compressing said introducer sleeve between jaws of a hinged clamp.

11. A method according to claim 9 wherein said compressing step comprises compressing said introducer sleeve by means of a first ramped member attached to said introducer sleeve and extending around a portion of the outer circumference of said sleeve, using a second ramped member slidable along said first ramped member.

12. A method according to claim 9 or claim 10 or claim 11 further comprising the step of latching said clamp to maintain compression around said introducer sleeve.

* * * * *